United States Patent [19]

Balbierz

[11] Patent Number: 4,840,613

[45] Date of Patent: Jun. 20, 1989

[54] PROTECTIVE SHEATH FOR CATHETER ASSEMBLY

[75] Inventor: Daniel J. Balbierz, Sunnyvale, Calif.

[73] Assignee: Menlo Care, Inc., Palo Alto, Calif.

[21] Appl. No.: 186,560

[22] Filed: Apr. 27, 1988

[51] Int. Cl.⁴ .............................................. A61M 5/00
[52] U.S. Cl. ..................................... 604/51; 604/163; 604/164; 604/171
[58] Field of Search ............... 604/171, 164, 165, 160, 604/163, 280

[56] References Cited

U.S. PATENT DOCUMENTS

| | | | |
|---|---|---|---|
| 4,175,564 | 11/1979 | Kwak | 604/171 |
| 4,392,853 | 7/1983 | Muto | 604/171 |
| 4,445,893 | 5/1984 | Bodicky | 604/165 |
| 4,581,025 | 4/1986 | Timmerimans | 604/164 X |
| 4,781,690 | 11/1988 | Ishida et al. | 604/280 X |

Primary Examiner—Stephen C. Pellegrino
Attorney, Agent, or Firm—Fliesler, Dubb, Meyer & Lovejoy

[57] ABSTRACT

An improvement in a catheter assembly including a cannula, an inserter having a guide channel therethrough in which the cannula slidably fits and a hub structure with the cannula proximal end portion attached to the hub structure. The improvement includes a sheath having a longitudinal slit or weakened portion and being about the cannula between the inserter and the hub structure. A sheath stripping construction carried by the inserter strips the sheath from about the cannula as the cannula slides distally through the guide channel. A first lock member is carried by the inserter and an interlocking second lock member is located about the cannula between the inserter and the hub structure. The cannula is protected from contamination and from kinking and a positive lock serves to prevent its accidental withdrawal. A method of inserting a cannula using such an assembly is likewise set forth.

18 Claims, 5 Drawing Sheets

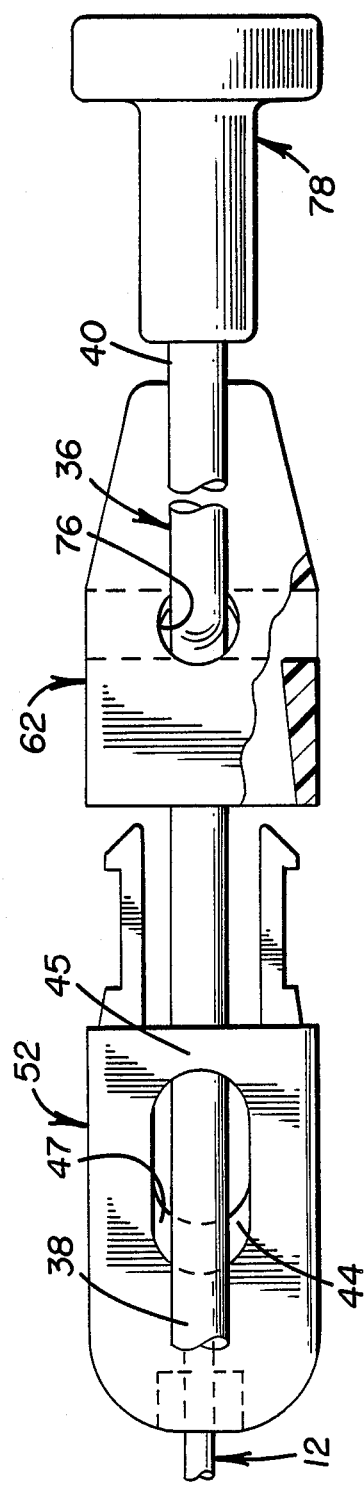
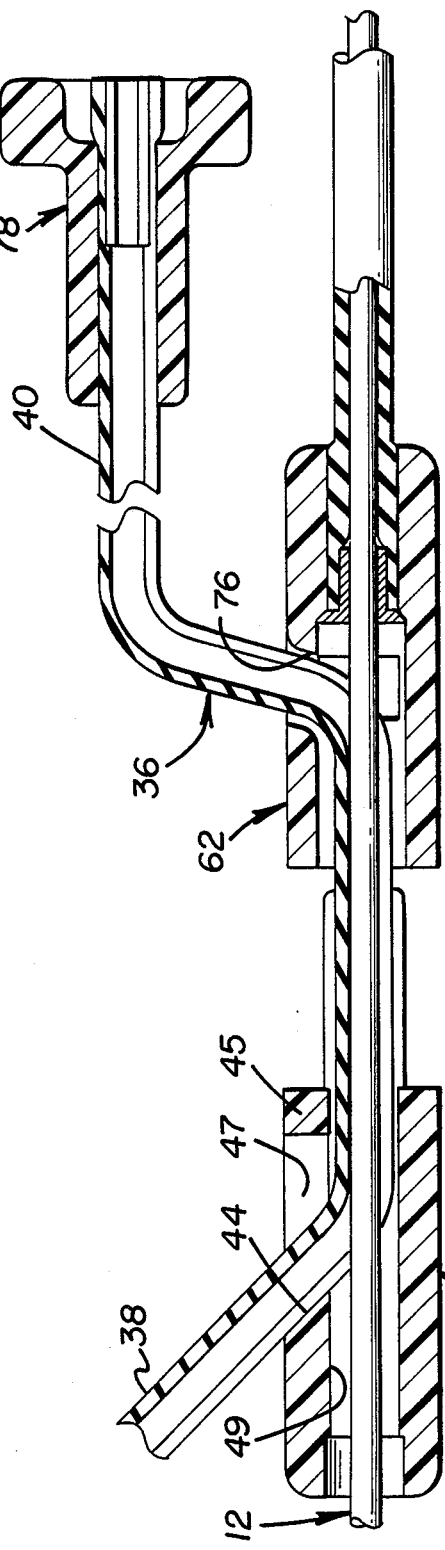
FIGURE 5
FIGURE 6

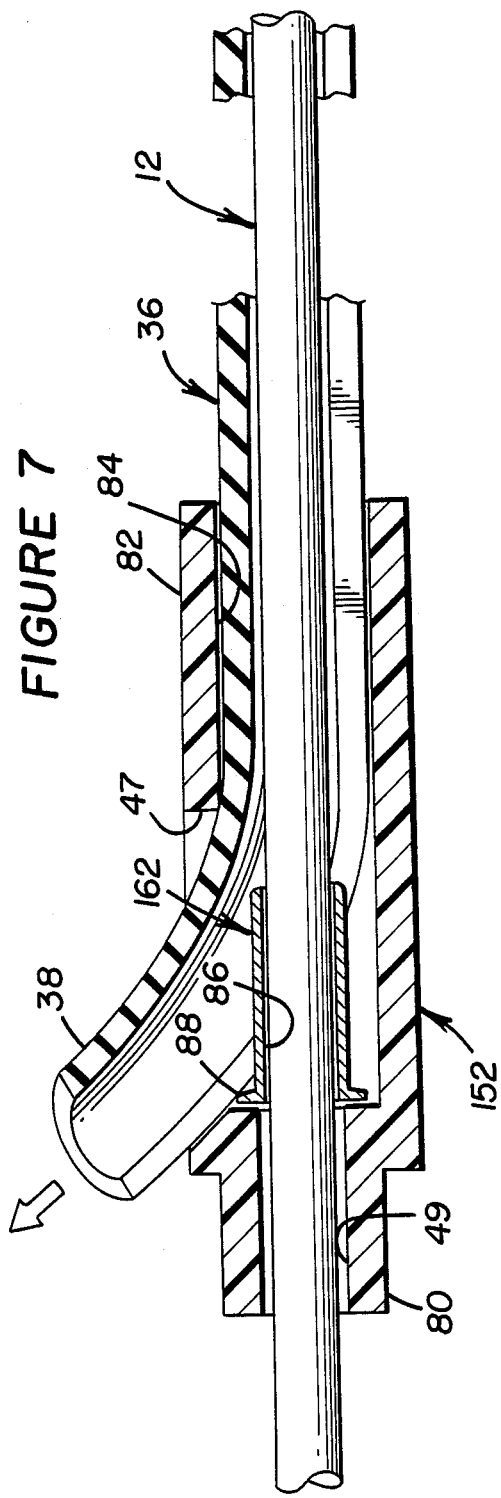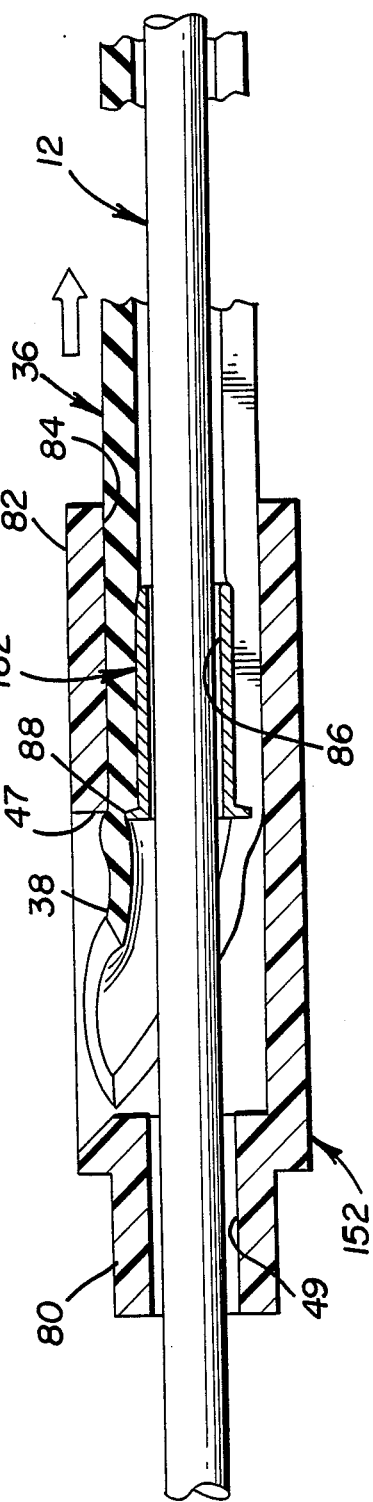

PROTECTIVE SHEATH FOR CATHETER ASSEMBLY

DESCRIPTION

1. Technical Field

The present invention relates to a catheter assembly and to a method for inserting a cannula useful for the introduction of nutrients and/or medications, or the extraction of fluids, from a living subject. The catheter assembly more particularly comprises a cannula, needle and catheter insert which allows the insertion of a selected length of cannula. The method particularly relates to a method of inserting a cannula into a living subject to a desired length.

2. Background of the Invention

A number of catheter assemblies are known for introduction of a polymeric cannula into a vein, artery or body cavity of a living subject for infusion or extraction of fluids.

In one method, a steel needle is sized to fit within the duct of a cannula and is inserted from the proximal end of the cannula so that the needle exits the distal end. The needle and cannula are then inserted into the living subject after which the needle is removed from the cannula, leaving the cannula behind with at least its distal end in the subject. Additional tubing can be attached thereto or medicaments or nutrients can be caused to flow through the cannula into the subject.

In order to prevent the needle from sliding relative to the cannula on insertion, several catheter inserters have been developed which aid the person inserting the cannula to prevent such sliding. This also provides a way to control the cannula without contaminating it. Inserters of a type comprising a positionally fixed device having a pair of winged members which when folded up will pinch the needle and prevent motion of the needle relative to the cannula and catheter inserter are known. Generally a relatively stiff cannula of a material to be inserted into the subject such as Teflon (trademark of DuPont) is fixed to the distal end of the inserter, while a flexible tubing (e.g., polyvinyl chloride) is attached to the proximal end of the inserter in flow communication with the cannula.

For example, in U.S. Pat. No. 4,194,504 a winged catheter inserter fixed to a cannula is described comprising a resilient tubular body having a lumen and a pair of wings having substantially uniform thickness such that on folding up of the wings, the lumen changes shape to capture the needle within for easier insertion. See also U.S. Pat. Nos. 4,198,973; 4,192,304; 4,192,305; 4,300,553; 4,388,074; 4,445,893; 4,353,369; and 4,326,519.

A difficulty with this type of winged inserter is that the length of cannula to be inserted is limited. The length is predetermined by the position that the inserter has been fixed on the cannula material. The winged inserters of the prior art have been attached to the cannula for a number of reasons including the need to secure cannula at one end of the inserter and flexible tubing at the other end and to prevent the relative movement of the inserter after use. Relatively long lengths of cannula cannot be used with this type of inserter because the inserter must be affixed relatively close to the distal end for accurate control of the cannula and only that portion extending from the distal end of the inserter may be used. Another difficulty with the fixed wing inserter is the desirability of being able to differ the length of the needle and the cannula for ease of insertion into the subject. A person inserting such cannulae, such as a nurse or doctor, will have varying preferences as to the positioning of the inserter relative to the needle and cannula end. This requires stocking several different sizes of cannula fabricated with differing distal end lengths.

One method of overcoming the difficulty of inserting a variable or relatively long length of cannula (greater than about 5 mm) has been to select a needle with an inner diameter greater than the outer diameter of the cannula. The needle is inserted into the subject and the cannula is fed through the needle into the subject to the desired length. This technique has several difficulties. First, the cannula for insertion must be stiff and/or have a reinforcing wire running through its duct during insertion. Also, when inserting such a device into an area such as a blood vessel, removal of the needle allows blood to escape around the insertion site or possible infection to enter through the insertion site which is larger than the cannula. After the cannula is in the desired position, the needle is generally removed. There is difficulty in removing the needle without further escape of blood or chance of infection. This is especially true when the cannula is attached to a hub portion which prevents sliding the needle off of the cannula's proximal end. If the needle is allowed to remain on the cannula there can be difficulty in preventing the sharpened edge of the needle from further piercing the subject or piercing the cannula. Bulky containment mechanisms are used to minimize but not eliminate this danger. The alternative to this type of method is direct surgical implantation of a cannula in the desired area which is both traumatic and costly.

More recently, as set out in co-pending application Ser. No. 826,439, filed Feb. 5, 1986, now U.S. Pat. No. 4,728,322 of Jack McClean Walker and Neil J. Sheenen, commonly assigned herewith, a catheter assembly has been set forth which solves a number of these problems. This assembly comprises a cannula, needle and catheter inserter wherein the inserter is in slidable relationship to the cannula and wherein the inserter or other device also serves to selectively restrict the needle from sliding relative to the inserter. The aforementioned application also relates to a method of inserting a cannula into a living subject using an inserter which is positioned such that the desired length of cannula for initial insertion extends beyond the inserter. The aforementioned application also sets forth a method which includes further inserting the cannula into the living subject after its initial insertion.

Another problem which exists with catheter assemblies wherein a portion of the cannula remains outside of the body is one of kinking. In such an instance, the flow of nutrients and/or medications into the body, and/or the flow of body fluids out through the cannula can be either restricted or completely cut-off with possibly disastrous effects for the patient. This problem is particularly acute in those instances wherein the cannula material is relatively soft, or perhaps softens on insertion into the living subject. Also, when a long section of cannula is to be inserted into the living subject, care must be used in maintaining sterility of the portion of the cannula initially positioned and extending proximally from the proximal end of the inserter. Contact of the cannula by the users fingers or the like would contaminate the cannula making it unsuitable for use in a living subject. One solution to this problem is to enclose the portion of the cannula that is to be handled in an axially collapsible cover, for example, a polyethylene bag of a very flexible material or a more rigid polymeric material with accordion type folds which allow axial collapsing, such that the cannula may be inserted further by handling the cover.

As also set forth in co-pending application Ser. No. 826,439, another solution to this problem is set forth in the nature of covering a portion of the cannula with an axially non-collapsible sheath. By axially non-collapsible is meant that when pushing in the cannula for further insertion, while also grasping the sheath, the sheath does not buckle or wrinkle or the like to an appreciable amount. The sheath, however, has walls which are of a relatively flexible material. The sheath has both a distal end and a proximal end. There is further a longitudinal slit at least a portion of the way through the wall of the sheath. In another embodiment the slit does not extend all the way through the wall of the sheath prior to removal to further aid in the protecting of the cannula. The cannula is positioned within the duct of the sheath in the area to be protected. The sheath is capable of being opened along the longitudinal slit and removed from the cannula. In one embodiment there is means aiding in the opening of the longitudinal slit. This means may be a part of the inserter and may serve to open the sheath during insertion of the cannula, or it can be an added device which opens the sheath during insertion. The sheath is preferably made of a polymeric material. Preferred polymeric materials include polyvinyl chloride (PVC), polyurethane, polyethylene and fluoroethylene propylene.

An axially non-collapsible sheath of the nature set forth in co-pending application Ser. No. 826,439 presents a number of advantages. However, once a desired length of cannula has been inserted and a portion of the sheath, or even all of the sheath, has been removed, there is still a region along the length of the cannula wherein kinking can occur. This area is that in between the inserter and the hub contacts the inserter. Another problem with such a sheath is that if too much of the sheath is removed (that is, if somewhat too much of the cannula is inserted in the blood vessel) it is very difficult to backoff the cannula and to reposition a portion of the sheath about the cannula proximal of the inserter. Yet another problem is that as the cannula is fed distally through the inserter it can become kinked if it is not fed directly axially forward, i.e., any angled force can lead to kinking. Further, in instances wherein the cannula can freely slide within the inserter, there is nothing to hold the cannula in position so that it will not advance inwardly into or proceed outwardly from the blood vessel.

The present invention is directed to overcoming one or more of the problems as set forth above.

DISCLOSURE OF INVENTION

In accordance with an embodiment of the present invention an improvement is set forth in a catheter assembly which has a cannula having distal and proximal end portions and a longitudinal duct from the distal to the proximal end portion. The assembly has an inserter having inserter distal and proximal end portions and a guide channel from the distal to the proximal end portion. The cannula slidably fits in the guide channel. A hub structure has a passageway therethrough and the cannula proximal end portion is attached to the hub structure with the duct in flow communication with the passageway. The improvement comprises a sheath having distal and proximal end portions and a longitudinal slit therethrough from the distal to the proximal end portion, the sheath being about the cannula between the inserter and the hub structure. Sheath stripping means are carried by the inserter and serve for stripping the sheath, starting from its distal end portion, from about the cannula as the cannula is moved distally through the guide channel. A first lock member is carried by the inserter and a second lock member is located about the cannula between the inserter and the hub structure. The first and second lock members are interlockable with one another.

In accordance with another embodiment of the present invention a method is set forth of inserting a cannula into a patient. A needle with a sharp insertion tip is positioned in the cannula of a catheter assembly as set forth above with the sharp insertion tip extending distally from the cannula distal end portion. The needle, along with the cannula distal end portion, is inserted in a patient. The needle is removed while leaving the cannula in the patient. The cannula is advanced the desired distance into the patient while simultaneously stripping the sheath from about the cannula at the inserter. The first and second lock members are locked together after the desired length of cannula has been advanced into the patient.

An improved catheter assembly and insertion method in accordance with the present invention protects the cannula from kinking over the entire distance between the inserter and the hub. Furthermore, in accordance with certain embodiments of the present invention a selected amount of the cannula may be fed through the inserter and into a blood vessel. Still further, if too much of the sheath is stripped off of the cannula, in accordance with an embodiment of the present invention it can be readily replaced over the cannula. And, in accordance with certain embodiments of the present invention, the sheath exerts a longitudinal force upon the cannula to pull it distally in a manner which does not lead to kinking of the cannula.

BRIEF DESCRIPTION OF DRAWINGS

The invention will be better understood by reference to the figures of the drawings wherein like numbers denote like parts throughout and wherein:

FIG. 5 illustrates, in partial plan view, still another alternate embodiment in accordance with the present invention;

FIG. 6 illustrates, in side partial view, partially in section, the embodiment of FIG. 5;

FIG. 7 illustrates, in side partial view, partially in section, another alternate embodiment yet of the subject invention; and FIG. 8 illustrates, in side partial view, partilly in section, the embodiment of FIG. 7 in its locked position.

BEST MODE FOR CARRYING OUT INVENTION

Figure 1:
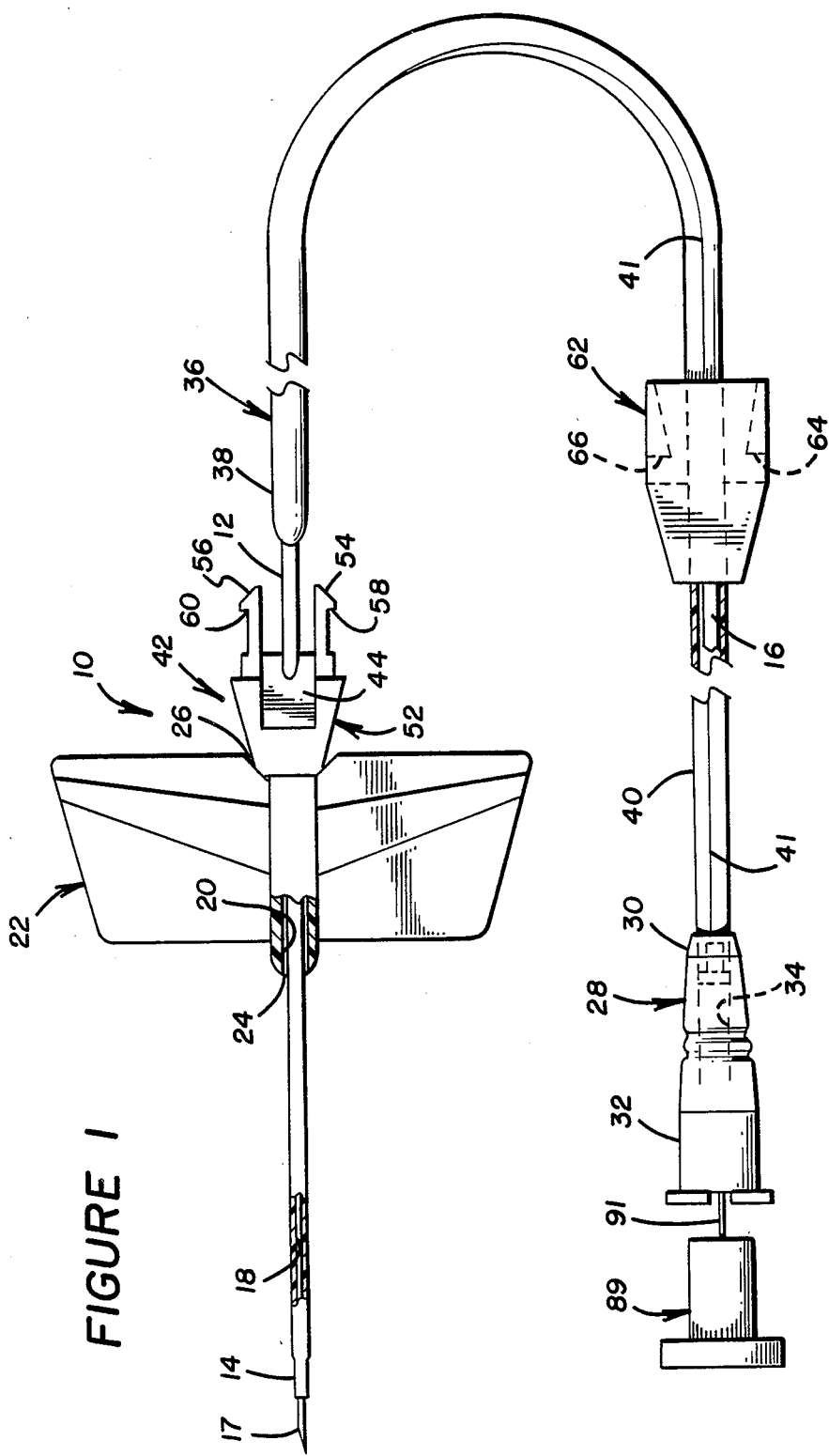
FIG. 1 illustrates, in plan view, partially in section, a catheter assembly in accordance with the an embodiment of the present invention.

The catheter assembly of the invention comprises a cannula of a desired or adjustable length, a sheath for protecting the cannula of the catheter assembly and a locking mechanism for ensuring that the sheath can be adequately positioned and locked in place to protect the cannula from kinking and accidental withdrawn. In a preferred embodiment, the catheter assembly comprises a cannula of a desired or adjustable length with an outer circumference which increases and/or of a material whose 2.5% Secant Modulus decreases when inserted in a patient.

The cannula of the invention can be of any material suitable for introduction into a living subject. Preferably, these materials are polymeric in nature and are selected to be sufficiently stiff for insertion such as fluorethylene propolyne (e.g., FEP-Teflon from DuPont) or the like. In general, the cannula should have a 2.5% Secant Modulus greater than about 20,000 N/cm$^2$ and preferably greater than about 28,000 N/cm$^2$ to prevent buckling or wrinkling upon insertion into the subject. Even more preferred are those compositions which soften or exhibit a decreased 2.5% Secant Modulus, for example, by exposure to liquids or upon insertion of the distal end portion of the cannula into the body of a living subject and its maintenance therein, or upon exposure to a temperature from about 20° C. to about 40° C. Particularly, preferred compositions absorb liquid (i.e., hydrate) and thereafter soften to a 2.5% Secant Modulus of less than 7,000 N/cm$^2$ which reduces the trauma to the surrounding tissues of the subject. The term softening ratio is used herein to refer to the ratio of the 2.5% Secant Modulus values of the composition selected in the form of a tubular cannula initially to the 2.5% Secant Modulus of the composition when softened. It is preferred that at least a portion of such compositions are hydrophilic. It is also preferred that the composition soften with a softening ratio of at least about 2:1.

Examples of softening polymers useful in the practice of the invention are those described in commonly assigned Co-pending application Ser. No. 780,543, filed Sept. 26, 1985, incorporated herein by reference. The preferred composition for the cannula comprises:

(a) a first phase which comprises a substantially non-hydrophilic polymeric component; and (b) a second phase which comprises a hydrophilic polymeric component;

said material (i) being capable of absorbing water to an extent that its softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant Modulus of less than about 7,000 N/cm$^2$.

Also useful are those softening polymers described in U.S. Pat. Nos. 4,359,558; 4,424,305; 4,454,309 and 4,439,583 of Tyndale Plains-Hunter Ltd. incorporated herein by reference. The preferred cannula composition essentially comprises a polyurethane diacrylate composition having from about 90 to about 65 weight percent of a hydrophilic polyurethane resin and from about 10 to about 35 weight percent of a diacrylate.

An alternative material which may be utilized as a cannula material is a thermoplastic composition with softenable and/or shaped-memory properties. Such polymeric compositions are described, for example, in the following articles: Softenable, Shape-Memory Thermoplastics for Biomedical Use, Robert S. Ward, M.D. 7 D, August 1985; and Thrombroresistant, Radioopaque, Softenable Thermoplastics Catheter Compound With Shape-Memory Properties, R. S. Ward, K. A. White, J. S. Riffle, Second World Congress On Biomaterials, 10th Annual Meeting Of The Society For Biomaterials, Washington, D.C., April 27–May 1, 1984. The aforementioned thermoplastic compositions comprise a base polymer that is a block or segmented copolymer thermoplastic with at least one block type with an abrupt effective glass transition temperature ($T_g$) at or greater than room temperature, but less than approximately body temperature. The remainder of the base polymer contains hard blocks whose dominant thermal transition is substantially greater than body temperature. The cannulae can also be made to expand and soften as follows. The cannulae are originally made with their eventually desired expanded internal diameter and then are heated above the glass transition temperature ($T_g$), drawn out to form longer and thinner cannulae and held in this state until cooled below the glass transition temperature. Once the longer and thinner cannulae have warmed to a temperature that is greater than room temperature but less than approximately body temperature, i.e., once the cannulae have reached the glass transition temperature, the shape-memory properties operate and the cannulae increase in internal and external diameter while shrinking in length.

It is also preferred when selecting such softening materials of the cannulae that such materials also swell wherein at least a portion of the cannula inner cross-section of the duct and/or outer circumference of the cannula increases to form an enlarged inner cross-section of the duct and/or enlarged outer circumference of the cannula when inserted in a living subject and maintained therein and/or when the duct is contacted by a liquid for a period of time sufficient for the enlarged duct cross-section and/or outer circumference to form. Preferably, the duct cross-section increases from about 25% to about 400%.

The composition of the cannula may be cross-linked if desired. Cross-linking give the composition strength wherein the melting or softening points of the uncrosslinked polymeric components permit sterilization of the catheter assembly using a cannula of such composition at above such temperature. Cross-linking of the material selected for the cannula may also be used to adjust the 2.5% Secant Modulus of the composition to a desired value. Cross-linking may also increase the tensile energy to break of the material which has been softened. Cross-linking can also be used to minimize extractable components of the composition.

Cross-linking can be effected by use of an appropriate cross-linking agent or by radiation, preferably in the presence of a cross-linking promoter, such as triallyl isocyanourate or the like. Or, the material can be cross-linked by high energy gamma or beta radiation.

The material of the cannula may contain additional ingredients such as stabilizers, antioxidants, radioopacifiers, medicaments, fillers or the like. For certain applications it may be advantageous to incorporate a water soluble or water dispersible medicament which can leach from the material when it contacts the fluids of the living subject. Such medicaments include antithrombogenic agents, antibiotics, antiviral agents, anticoagulants, antiinflamatory agents, and the like.

A cannula selected such that it swells or softens should not do so appreciable during the time it is being inserted in a living subject or the like. It is preferable that such cannulae's swelling or softening time should be at least about 15 seconds and preferably at least about 60 seconds. The swelling of the cannula has several advantages. Swelling of the cannula permits insertion of a smaller device for equivalent fluid flow and/or can result in pressure around a wound site reducing bleeding and bacterial invasion into the wound and prevent catheter slip out, a common cause for changing catheters prematurely. Increased cross-section of the cannula duct also permits increased flow through the cannula when compared with similar non-swelling cannula of identical initial dimensions. This allows access to smaller areas such as the veins in the limbs and easier insertion into the selected site. Further, swelling of the cannula may increase the outer circumference sufficiently that it becomes as great as the diameter of the inserted channel. After insertion of the cannula this may be desirable. The inserter then looses its ability to slide relative to the cannula and needle due to the pressure of the cannula against the inserted channel. This is advantageous in preventing relative movement of the cannula and inserter. Once the inserter is attached (e.g., by taping) to the subject, further movement of the cannula in or out of the subject is limited. Cannulae which become soft are also advantageous. A soft cannula tends to cause less irritation to the intima (lining of the vein) and to the insertion site and is less likely to contribute to mechanical phlebitis. The softness of the cannula also permits it to float in a vein rather than lie on the point where inserted and consequently any infusion is delivered evenly helping to avert chemical phlebitis.

Once the cannula is selected, a needle is selected having distal and proximal ends and having a sharpened insertion tip at the distal end. The needle may be selected to be either hollow or solid, that is, the term needle is used broadly to include hollow or solid longitudinal piercing members. The needle is positioned within the distal end portion of the longitudinal duct of the cannula with the insertion tip extending beyond the distal end of the cannula. An extraction wire, rod, etc., may optionally be attached to the proximal end of the needle and extend outward to the proximal end of the cannula. Extraction of the needle may be accomplished by pulling the extraction wire. Alternatively, the proximal end of needle may extend beyond the inserter toward the proximal end of the cannula for ease of extraction.

Further, a catheter inserter having distal and proximal ends and having a cannula guide channel extending from its distal end to its proximal end can have a cannula positioned in slidable relationship through the channel such that the distal end portion of the cannula extends beyond the distal end of the channel. Means are provided for selectably restricting the cannula and needle from sliding relative to the channel. In a preferred embodiment the catheter inserter comprises a body having a pair of members extending therefrom, the members being movable to selectably restrict the cannula and needle from sliding relative to the channel. It is preferred that the body have a pair of flexible wing members extending therefrom, the wings being foldable upwardly together to selectably restrict the cannula and needle from sliding relative to the channel. The members can be moved from a relaxed position to a tense position to selectably restrict the cannula and needle from sliding relative to the channel. The body of the catheter insert preferably has a bore extending from the distal to the proximal end of the inserter and which serves as the guide channel. The diameter of the guide channel is preferably at least equal to or slightly greater than the outer circumference of the cannula. In any event, the cannula and channel are such that the cannula can be positioned in slidable relationship to the channel. The preferred cannula inserters resemble the wing inserters of the prior art but have relatively larger longitudinal bores and comprise a continuous cannula extending beyond the distal end of the inserter to beyond the proximal end of the inserter to allow a slidable relationship with the cannula. Other inserters can include tubular devices with an enlarged bore for positioning the cannula and an area which can be manually squeezed, have a hose clamp attached thereover, or have means tightened thereon to restrict the cannula from sliding relative to the channel. Another method of obtaining the slidable relationship is to use an inserter such as a spring which is normally closed and prevents the slidable relationship and must be opened to achieve the slidable relationship.

The catheter assembly of the invention is useful for inserting a cannula into a living subject. Preferably, the cannula is inserted in a blood vessel or cavity. The preferred use of the catheter assembly is for intravenous (IV) use. By living subject is meant any living thing, e.g., mammal, reptile, fish, etc., for which fluids are necessary to infuse or drain. In particular, the assembly is useful in mammals, specifically horses, cattle, dogs, cats and humans. The catheter assembly may be used to infuse or drain liquids or to hook or connect to other apparatus or devices or can be used to position sensors or the like.

The catheter assembly further comprises a cannula hub portion. The hub portion has a passageway therethrough from the proximal end portion to the distal end portion of the hub and has appropriate attaching means for attaching the proximal end portion of the cannula to the distal end portion of the hub with the passageway in flow communication with the duct in the proximal end portion of the cannula. Many such hubs are known in the prior art and are suitable for the invention. Where the cannula material is a swellable material it is desirable to have a hub assembly which will prevent restriction of flow in cannula and will accommodate the expansion. One such hub is described in commonly assigned patent application Ser. No. 788,461 filed Oct. 17, 1985, incorporated herein by reference.

A better understanding of the invention will follow from a discussion of the figures.

FIG. 1 illustrates a catheter assembly 10 having a cannula 12 having cannula distal and proximal end portions 14 and 16. The cannula 12 is about a needle 17. A longitudinal duct 18 runs through the cannula 12 from the cannula distal end portion 14 to the cannula proximal end portion 16.

The cannula 12 fits in a guide channel 20 of an inserter 22 having an inserter distal end portion 24 and an inserter proximal end portion 26. The guide channel 20 extends through the inserter 22 from the inserter distal end portion 24 to the inserter proximal end portion 26. The cannula 12 fits slidably within the guide channel 20.

A hub structure 28 has a hub distal end portion 30 and a hub proximal end portion 32. The hub structure 28 also has a passageway 34 therethrough from the hub distal end portion 30 to the hub proximal end portion 32.

The cannula proximal end portion 16 is attached to the hub structure 28 with the duct 18 in flow communication with the passageway 34.

In accordance with the present invention, a sheath 36 is provided having a sheath distal end portion 38 and a sheath proximal end portion 40. A longitudinal slit 41 extends along the sheath 36 from the sheath distal end portion 38 to the sheath proximal end portion 40. The slit 41 need not initially extend all the way through the sheath 36 but may instead, if desired, either extend only partially therethrough but sufficiently so that the sheath 36 can be stripped as explained below or be a weakened longitudinal portion thereof so that the sheath 36 can be so stripped. As such stripping occurs the slit 41 will thereafter extend all the way through the sheath 36. The sheath 36 is located about the cannula 12 between the inserter 22 and the hub structure 28.

Figure 2:
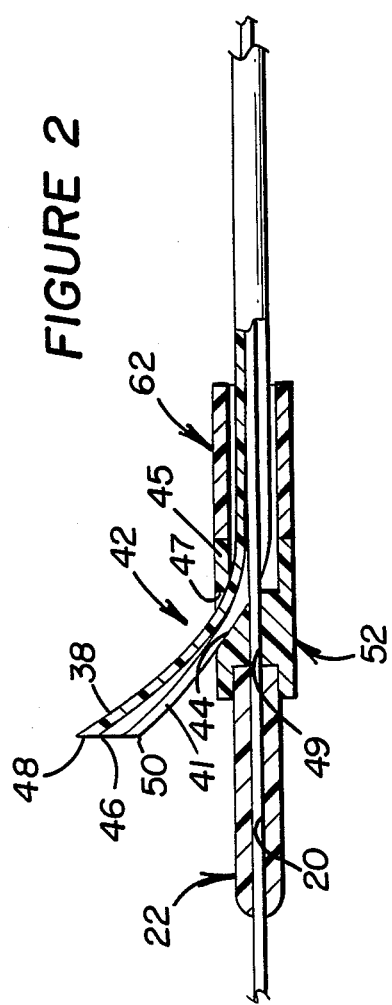
FIG. 2 illustrates, in side partial view, partially in section, a detail in a modification of the structure shown in FIG. 1.

Sheath stripping means 42 are provided, carried by the inserter 22 and serve for stripping the sheath 36, starting from its distal end portion 38, from about the cannula 12 as the cannula 12 is slid distally through the guide channel 20. In the particular embodiments illustrated in FIGS. 1 and 2 the sheath stripping means 42 is in the nature of a ramp 44 carried by a first lock member 52. It is preferred that a bridge 45 (not in the embodiment illustrated in FIG. 1) extend across the first lock member 52 above or slightly proximally of the ramp 44 and leaving an opening 47 through which the sheath 36 can exit, the bridge 45 serving to cause the sheath 36 (and the cannula 12) to move longitudinally distally to where the cannula 12 enters an extension 49 of the guide channel 20 formed in the first lock member 52.

The sheath distal end portion 38 can be cut back at an angle to its longitudinal axis to form a cutback area 46 having a distal apex 48 towards the inserter 22 and a proximal base 50 towards the hub structure 28. The longitudinal slit 41 terminates at the base 50 whereby proper alignment is assured. The sheath stripping means 42 comprises the ramp 44 positioned to receive the cutback area 46 and to direct the sheath distal end portion 38 outwardly from the cannula 12 as the sheath 36 is moved distally.

The first lock member 52 is carried by the inserter 22. It can be of separate construction or it can be integral with the inserter 22. The first lock member 52 includes a pair of tines 54, 56 (see FIG. 1) which extend towards the hub structure 28. In the particular embodiment illustrated the tines 54, 56 define respective ledges 58, 60 for interlocking with a second lock member 62. The second lock member 62 fits about the cannula 12 between the inserter 22 and the hub structure 28. Basically, the tines 54, 56 are made of a material which has a reasonable amount of elasticity whereby when the tines 54, 56 are pushed within the second lock member 62 they are first forced somewhat towards one another and then spring back outwardly to lock in appropriate cavities 64, 66. In this manner a solid binding together is provided of the first lock member 52 with the second lock member 62.

In accordance with the embodiment illustrated in FIG. 1, the second lock member 62 is slidably positioned about the sheath 36. In this embodiment the proximal end portion 40 of the sheath 36 is suitably attached to the hub structure 28 so as to prevent kinking of the cannula 12 proximal of the second lock member 62. Also in accordance with the embodiment of FIG. 1, the second lock member 62 is free of connection with the hub structure 28. This allows the second lock member 62 to be slidingly moved along the sheath 36 and to be interlocked with the first lock member 52.

In practice, the cannula 12 is fed through the inserter 22 to a desired length while the sheath 36 is stripped by the sheath stripping means 42, starting from the sheath distal end portion 38, from about the cannula 12 as the cannula 12 is slid distally through the guide channel 20 in the inserter 22. Once a desired length of cannula 12 has been fed into the patient, the second lock member 62 is interlocked with the first lock member 52. The remaining portion of the sheath 36, specifically the proximal end portion 40 thereof, extends proximally of the second lock member 62 and continues to protect the cannula 12 from kinking. The excess of the sheath distal end portion 38 can be simply snipped off.

Furthermore, should somewhat too much of the distal end portion 38 of the sheath 36 be stripped off of the cannula 12 by the sheath stripping means 42, the sheath 36 can be pulled backwardly through the second lock member 62 whereby the retracted portion of the cannula 12 is again covered by the sheath 36 due to the tight but sliding fit of the second lock member 62 about the sheath 36. The bridge 45 (when present) also aids in the recovering of the retracted portion of the cannula 12. In essence, the cannula 12 is simply forced through the longitudinal slit 41 during this procedure. Thus, the second lock member 62 can be of a construction sufficient to reposition portions of the sheath 36 distal of the second lock member 62 about the cannula 12 as the second lock member 62 is slid towards the inserter 22 or as the cannula 22 and sheath 36 are moved proximal relative to the second lock member 62. Generally the second lock member 62 is designed so that when it is locked into position with the first lock member 52 the sheath 36 is restricted from further motion. This provides protection from accidental withdrawal of the cannula 12 when personnel are manipulating the hub structure 28 during routine usage of the device. This is accomplishable by working with sufficiently close tolerances, e.g., in the opening 47 relative to the ramp 44.

It is worthwhile to note that if the catheter 12 and the sheath 36 are moved relatively towards the second lock member 62 in order to replace a length of the sheath 36 about a corresponding length of the cannula 12, then the cannula 12 is completely enclosed thereby preventing any body fluids thereon from contacting a medical worker. This is important in protecting against infection of medical personnel.

Figure 3:
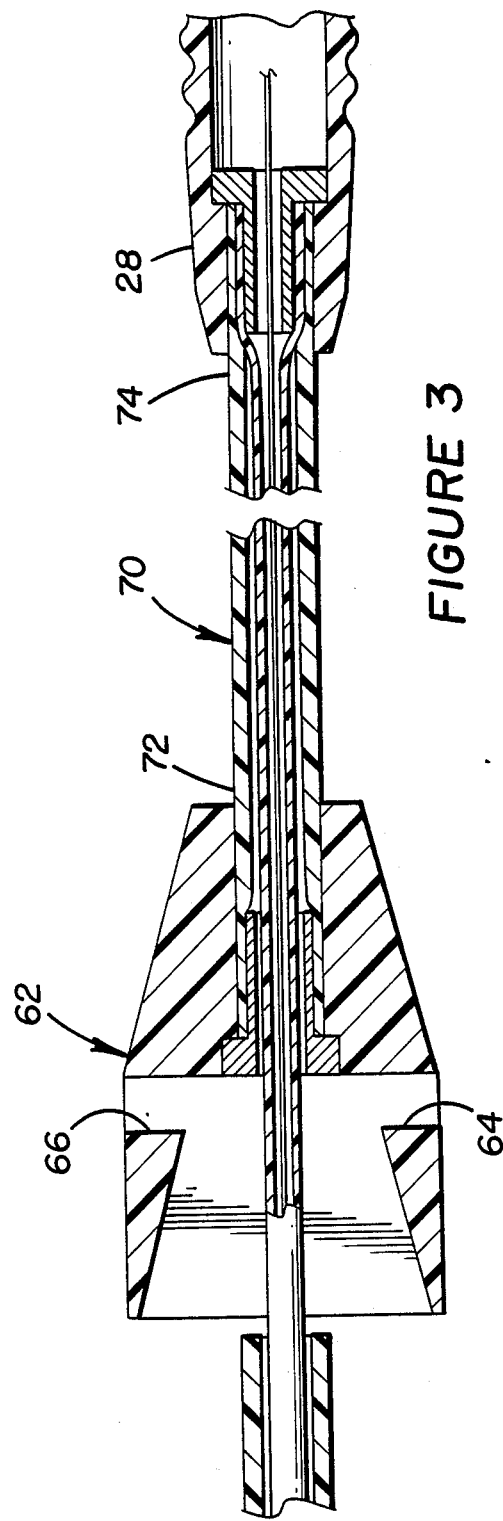
FIG. 3 illustrates, in partial plan view, partially in section, an alternate embodiment in accordance with the present invention.

FIG. 3 illustrates an embodiment of the present invention wherein the second lock member 62 is connected to the hub structure 28. In this embodiment a sleeve 70 is located about the cannula 12 between the second lock member 62 and the hub structure 28. The sleeve 70 has a distal end portion 72 and a proximal end portion 74. The sleeve distal end portion 72 is attached to the second lock member 62 and the sleeve proximal end portion 74 is attached to the hub structure 28 thereby connecting the second lock member 62 to the hub structure 20.

Figure 4:
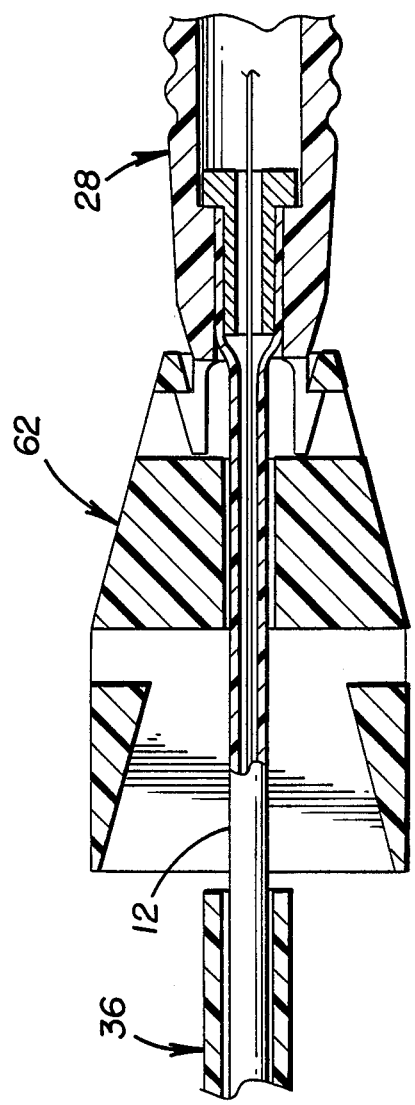
FIG. 4 illustrates, in a view similar to FIG. 3, another alternate embodiment of the invention.

It is also possible, as shown in FIG. 4, to directly attach the second lock member 62 to the hub structure 28 and eliminate the need for the sleeve 70. Or, the second lock member 62 can be made a part of the hub structure 28. A simple snap on fit is shown in FIG. 4. However, in operation it is generally more convenient to use the sleeve 70.

FIGS. 5 and 6 illustrate an embodiment of the present invention wherein the sheath distal end portion 38 normally extends at least a slight distance through the opening 47 defined by the ramp 44 and the bridge 45. To advance the sheath 36 distally one pulls upon the distal end portion 38 thereof and the sheath 36, as it is moved distally and more and more of it extends through the opening 47, also moves the cannula 12 distally with the force exerted upon the cannula 12 being longitudinal and in line with the extension 49 of the guide channel 20. In this manner, the cannula 12 is not subjected to off axis forces which might cause it to kink when being advanced distally. Note that the second lock member 62 is pulled distally by pulling upon the distal end portion 38 of the sheath 36. This is accomplished by bringing the sheath proximal end portion 40 laterally through an opening 76 in the second lock member 62 and by having a blocking member 78 attached to the sheath proximal end portion 40, the blocking member 78 being of sufficient size to prevent the entire sheath proximal end portion 40 from passing through the opening 76. Or, the second lock member 62 can be otherwise attached to move distally with the sheath 36.

After the sheath 36 has been moved distally as far as possible the second lock member 62 interlocks with the first lock member 52 in the same manner as the lock members 52 and 62 of FIG. 1 interlock. Once the interlocking has been completed the user pulls upon the locking member 78 whereby the sheath 36 is pulled proximally through the openings 47 and 76 until it is entirely removed through the opening 76. The entire procedure serves to protect the cannula 12 from contact with the fingers of the person advancing the cannula 12 into the patient. Or, the sheath 36 can be snipped off if it is directly connected to the second lock member 62. Also, proper alignment of the force supplied to the cannula 12 to move it distally ensures that the cannula 12 does not kink during such movement. And, the essentially automatic retraction of the sheath 36 utilizing the blocking member 78 provides a final very neat package which has no projecting portions of the sheath 36.

FIGS. 7 and 8 illustrate another embodiment of the present invention. The embodiment of FIGS. 7 and 8 utilizes a significantly different locking structure. In particular, FIGS. 7 and 8 illustrate the use of a first locking member 152 along with a second locking member 162, as illustrated. The first locking member 152 has a proximal end portion 80 which is attached to the inserter 22 (not illustrated in FIGS. 7 and 8). The first lock member includes the extension 49 of the guide channel 20 in the inserter 22. A proximal end portion 82 of the first lock member 152 has a bore 84 having a diameter only slightly greater than the outside diameter of the sheath 36. In this manner, the sheath 36 can be pulled forwardly (leftwardly) through the bore 84 without binding therein.

FIG. 7 illustrates the situation wherein the sheath 36 is being pulled distally by having its distal end 38 pulled upon. In this situation the cannula 12 is pulled distally along with the sheath 36 and proceeds into the extension 49 of the guide channel 20. Note that the second locking member 162 is carried leftwardly in FIG. 7 during this operation and takes no part in the operation.

The second lock member 162 is in the nature of a hollow rivet or eyelet having a central bore 86. The central bore 86 is large enough so that the cannula 12 can slide freely therethrough. The eyelet 162 may suitably includes an outflaring annular flange 88 extending outwardly from its distal end portion 90 although such is not essential to its operation. The outer diameter of the eyelet 162 is larger than the inner diameter of the sheath 36, and, further, the separation between the outer diameter of the eyelet 162 and the diameter of the bore 84 is generally less than the thickness of the sheath 36. In this manner, once sufficient of the sheath 36 has been advanced as illustrated in FIG. 7 one can then pull the sheath 36 proximally while holding on to the first lock member 152 whereby the eyelet 162 is propelled, through its contact with the inside diameter of the sheath 36, in a distal direction until it lodges in the bore 84.

Basically, the sheath 36 becomes sandwiched between the eyelet 162 and the bore 84 and, indeed, is generally compressed into a locking fit. Preferably the flange 88 aids in this locking fit in providing additional compression of the sheath 36 between the bore 84 and the eyelet 162 between the flange 88 and the bore 84. This occurs if the outer diameter of the flange 88 is less than the inner diameter of the bore 84. The remaining portion of the sheath 36, that is, that portion of the sheath 36 which has been removed distally through the opening 47, may be merely cut or snipped off. Any attempts to pull on the sheath 36 in a distal direction will only serve to more tightly wedge or lock the eyelet 162 to the first lock member 152.

In use the catheter assembly 10 is arranged with the needle 17 in place. The needle 17, along with the distal end portion 14 of the cannula 12 is inserted into a patient, e.g., into a blood vessel. The needle 17 is removed from the catheter assembly 10 (by pulling on knob 89 (FIG. 1) attached to a wire 91 which is attached to the needle 17) while leaving the cannula 12 in the patient. The cannula 12 is advanced a desired distance into the patient while the sheath 36 is simultaneously stripped, at its distal end portion 38, from about the cannula 12 at the inserter 22. The first lock member 52 (or 152) is interlocked with the second lock member 62 (or 162) after the desired length of cannula 12 has been advanced into the patient.

INDUSTRIAL APPLICABILITY

The present invention sets forth a catheter assembly 10 wherein the cannula 12 exterior of the body is protected from kinking proximally of the inserter 22. Furthermore, in accordance with certain embodiments of the invention the length of the cannula 12 inserted in the body can be adjusted somewhat, as by withdrawing any excess length which has been inserted, and any backed up length of cannula is immediately resheathed to protect against infection to medical personnel. Furthermore, in accordance with certain embodiments of the current invention the cannula is protected from accidental withdrawal by the locking of the first lock member 52 and the second lock member 62.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. In a catheter assembly having a cannula having cannula distal and proximal end portions and a longitudinal duct therethrough from the cannula distal end portion to the cannula proximal end portion, an inserter having inserter distal and proximal end portions and a guide channel therethrough from the inserter distal end portion to the inserter proximal end portion, the cannula slidably fitting in the guide channel, and a hub structure having hub distal and proximal end portions and a passageway therethrough from the hub distal end portion to the hub proximal end portion, the cannula proximal end portion being attached to the hub structure with the duct in flow communication with the passageway, an improvement comprising:

a sheath having sheath distal and proximal end portions and a longitudinal slit or weakened portion extending therealong from said sheath distal end portion to said sheath proximal end portion, said sheath being about said cannula between said inserter and said hub structure;

sheath stripping means carried by said inserter for stripping said sheath, starting from said sheath distal end portion, from about said cannula as said cannula is slid distally through said guide channel;

a first lock member carried by said inserter; and a second lock member about said cannula between said inserter and said hub structure, said first and second lock members being interlockable with on another.

2. A catheter assembly as set forth in claim 1, further characterized in that said second lock member is carried by said hub structure.

3. A catheter assembly as set forth in claim 2, further including:

a sleeve having sleeve distal and proximal end portions, said sleeve being about said cannula between said second lock member and said hub structure with said sleeve distal end portion attached to said second lock member and with said sleeve proximal end portion attached to said hub structure.

4. A catheter assembly as set forth in claim 2, wherein said second lock member is directly attached to said hub structure.

5. A catheter assembly as set forth in claim 1, wherein said sheath distal end portion is cut back at an angle to a longitudinal axis thereof to form a cut back area having an apex towards said inserter and a base towards said hub structure, said longitudinal slit or weakened portion terminating at said base; and wherein said sheath stripping means comprises a ramp positioned to slidingly receive said cut back area and to direct said sheath distal end portion outwardly away from said cannula as said sheath is moved distally.

6. A catheter assembly as set forth in claim 1, further characterized in that said second lock member is slidably positioned about said sheath.

7. A catheter assembly as set forth in claim 6, wherein said second lock member is of a construction sufficient to reposition portions of said sheath distal of said second lock member about said cannula as said second lock member moves distally relative to said sheath and said cannula.

8. A catheter assembly as set forth in claim 6, wherein said sheath distal end portion is cut back at an angle to a longitudinal axis to form a cut back area having an apex towards said inserter and a base towards said hub structure, said longitudinal slit or weakened portion terminating at said base; and wherein said sheath stripping means comprises a ramp positioned to slidingly receive said cutback area and to direct said sheath distal end portion outwardly away from said cannula as said sheath is moved distally.

9. A catheter assembly as set forth in claim 6, wherein said second lock member is free of connection with said hub structure.

10. A catheter assembly as set forth in claim 9, wherein said second lock member is of a construction sufficient to reposition portions of said sheath distal of said second lock member about said cannula as said second lock member moves distally relative to said sheath and said cannula.

11. A catheter assembly as set forth in claim 10, wherein said sheath distal end portion is cut back at an angle to a longitudinal axis to form a cut back area having an apex towards said inserter and a base towards said hub structure, said longitudinal slit or weakened portion terminating at said base; and wherein said sheath stripping means comprises a ramp positioned to slidingly receive said cut back area and to direct said sheath distal end portion outwardly away from said cannula as said sheath is moved distally.

12. A catheter assembly as set forth in claim 9, further including:

means for preventing withdrawal of the sheath upon interlocking of said first and second lock members.

13. A catheter assembly as set forth in claim 1, wherein said sheath stripping means comprises a ramp positioned to slidingly receive said sheath distal end portion and to direct said sheath distal end portion outwardly away from said cannula as said sheath is moved distally and further including:

a bridge above or slightly proximal of said ramp and defining an opening between said ramp and said bridge through which said sheath passes.

14. A catheter assembly as set forth in claim 13, wherein said second lock member is carried by said hub structure and includes an opening therethrough, wherein said sheath proximal end portion passes through said opening and further including:

means for preventing said sheath proximal end portion from moving through said opening as said sheath is move distally.

15. A catheter assembly as set forth in claim 14, wherein said preventing means comprises a member attached to said sheath proximal end portion, said member being larger than said opening.

16. A catheter assembly as set forth in claim 1, wherein said first lock member includes a bore in close but sliding fit about said sheath, said bore being defined by a bridge slightly proximal of said ramp; and wherein said second lock member comprises an eyelet having an outer diameter greater than an inner diameter of said sheath and less than the diameter of said bore, said second lock member being located about said cannula within said first lock member 17. A catheter assembly as set forth in claim 16 wherein said eyelet includes a distal end portion having a flange extending outwardly therefrom, the outer diameter of said flange being less than the inner diameter of said bore.

18. A method of inserting a cannula into a patient, comprising:

(a) positioning a needle with a sharp insertion tip in the cannula of the catheter assembly of claim 1 with the sharp insertion tip extending distally from the cannula distal end portion;

(b) inserting the needle along with the cannula distal end portion in a patient;

(c) removing said needle while leaving said cannula in said patient;

(d) advancing the cannula a desired distance into the patient while simultaneously stripping said sheath from about said cannula at said inserter; and (e) locking said first and second lock members together after said desired length of cannula has been advanced into the patient.

* * * * *

REEXAMINATION CERTIFICATE (2069th)

United States Patent
[11] B1 4,840,613

Balbierz

[45] Certificate Issued Jul. 27, 1993

[54] PROTECTIVE SHEATH FOR CATHETER ASSEMBLY

[75] Inventor: Daniel J. Balbierz, Sunnyvale, Calif.

[73] Assignee: Menlo Care, Inc., Palo Alto, Calif.

Reexamination Request:
No. 90/002,800, Jul. 30, 1992

Reexamination Certificate for:
Patent No.: 4,840,613
Issued: Jun. 20, 1989
Appl. No.: 186,560
Filed: Apr. 27, 1988

[51] Int. Cl.$^5$ ............................................. A61M 5/00
[52] U.S. Cl. ................................... 604/51; 604/163; 604/164; 604/171
[58] Field of Search ............... 604/164, 165, 171, 160, 604/163, 280

[56] References Cited

U.S. PATENT DOCUMENTS 3,786,810 1/1974 Pannier, Jr. et al. ............... 604/158
4,175,564 11/1979 Kwak .................. 604/171
4,392,853 7/1983 Muto .................. 604/171
4,445,893 5/1984 Bodicky ............... 604/165
4,581,025 4/1986 Timmermans ............ 604/164
4,781,690 11/1988 Ishida et al. ............ 604/280

*Primary Examiner*—Paul J. Hirsch

[57] ABSTRACT

An improvement in a catheter assembly including a cannula, an inserter having a guide channel therethrough in which the cannula slidably fits and a hub structure with the cannula proximal end portion attached to the hub structure. The improvement includes a sheath having a longitudinal slit or weakened portion and being about the cannula between the inserter and the hub structure. A sheath stripping construction carried by the inserter strips the sheath from about the cannula as the cannula slides distally through the guide channel. A first lock member is carried by the inserter and an interlocking second lock member is located about the cannula between the inserter and the hub structure. The cannula is protected from contamination and from kinking and a positive lock serves to prevent its accidental withdrawal. A method of inserting a cannula using such an assembly is likewise set forth.

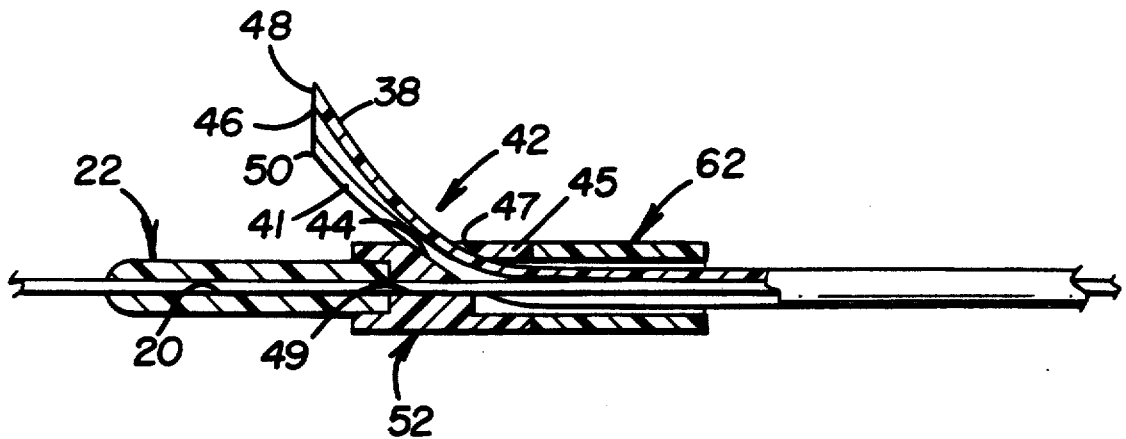

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-18 is confirmed.

New claims 19-36 are added and determined to be patentable.

19. *In a catheter assembly having a cannula having cannula distal and proximal end portions and a longitudinal duct therethrough from the cannula distal end portion to the cannula proximal end portion, a needle having a sharp point, said needle being within and in slidable relation to said duct at said cannula distal end portion, said sharp point extending distally from said cannula distal end portion, means for withdrawing said needle fully proximally through said duct, an inserter having inserter distal and proximal end portions and a guide channel therethrough from the inserter distal end portion to the inserter proximal end portion, the cannula slidably fitting in the guide channel, and a hub structure having hub distal and proximal end portions and a passageway therethrough from the hub distal end portion to the hub proximal end portion, the cannula proximal end portion being attached to the hub structure with the duct in flow communication with the passageway, an improvement comprising:*

*a sheath having sheath distal and proximal end portions and a longitudinal slit or weakened portion extending therealong from said sheath distal end portion to said sheath proximal end portion, said sheath being about said cannula between said inserter and said hub structure;*

*sheath stripping means carried by said inserter for stripping said sheath, starting from said sheath distal end portion, from about said cannula as said cannula, after said needle has been fully withdrawn proximally through said duct, is slid distally through said guide channel;*

*a first lock member carried by said inserter; and*

*a second lock member about said cannula between said inserter and said hub structure, said first and second lock members being interlockable with one another.*

20. *A catheter assembly as set forth in claim 19, further characterized in that said second lock member is carried by said hub structure.*

21. *A catheter assembly as set forth in claim 20, further including:*

*a sleeve having sleeve distal and proximal end portions, said sleeve being about said cannula between said second lock member and said hub structure with said sleeve distal end portion attached to said second lock member and with said sleeve proximal end portion attached to said hub structure.*

22. *A catheter assembly as set forth in claim 20, wherein said second lock member is directly attached to said hub structure.*

23. *A catheter assembly as set forth in claim 19, wherein said sheath distal end portion is cut back at an angle to a longitudinal axis thereof to form a cut back area having an apex towards said inserter and a base towards said hub structure, said longitudinal slit or weakened portion terminating at said base; and*

*wherein said sheath stripping means comprises a ramp positioned to slidingly receive said cut back area and to direct said sheath distal end portion outwardly away from said cannula as said sheath is moved distally.*

24. *A catheter assembly as set forth in claim 19, further characterized in that said second lock member is slidably positioned about said sheath.*

25. *A catheter assembly as set forth in claim 24, wherein said second lock member is of a construction sufficient to reposition portions of said sheath distal of said second lock member about said cannula as said second lock member moves distally relative to said sheath and said cannula.*

26. *A catheter assembly as set forth in claim 24, wherein said sheath distal end portion is cut back at an angle to a longitudinal axis to form a cut back area having an apex towards said inserter and a base towards said hub structure, said longitudinal slit or weakened portion terminating at said base; and*

*wherein said sheath stripping means comprises a ramp positioned to slidingly receive said cutback area and to direct said sheath distal end portion outwardly away from said cannula as said sheath is moved distally.*

27. *A catheter assembly as set forth in claim 24, wherein said second lock member is free of connection with said hub structure.*

28. *A catheter assembly as set forth in claim 27, wherein said second lock member is of a construction sufficient to reposition portions of said sheath distal of said second lock member about said cannula as said second lock member moves distally relative to said sheath and said cannula.*

29. *A catheter assembly as set forth in claim 28, wherein said sheath distal end portion is cut back at an angle to a longitudinal axis to form a cut back area having an apex towards said inserter and a base towards said hub structure, said longitudinal slit or weakened portion terminating at said base; and*

*wherein said sheath stripping means comprises a ramp positioned to slidingly receive said cut back area and to direct said sheath distal end portion outwardly away from said cannula as said sheath is moved distally.*

30. *A catheter assembly as set forth in claim 27, further including:*

*means for preventing withdrawal of the sheath upon interlocking of said first and second lock members.*

31. *A catheter assembly as set forth in claim 19, wherein said sheath stripping means comprises a ramp positioned to slidingly receive said sheath distal end portion and to direct said sheath distal end portion outwardly away from said cannula as said sheath is moved distally and further including:*

*a bridge above or slightly proximal of said ramp and defining an opening between said ramp and said bridge through which said sheath passes.*

32. *A catheter assembly as set forth in claim 31, wherein said second lock member is carried by said hub structure and includes an opening therethrough, wherein said sheath* proximal end portion passes through said opening and further including:

means for preventing said sheath proximal end portion from moving through said opening as said sheath is moved distally.

33. A catheter assembly as set forth in claim 32, wherein said preventing means comprises a member attached to said sheath proximal end portion, said member being larger than said opening.

34. A catheter assembly as set forth in claim 19, wherein said first lock member includes said sheath stripping means, said sheath stripping means comprising a ramp positioned to slidingly receive said sheath distal end portion and to direct said sheath distal end portion outwardly away from said cannula as said sheath is moved distally, said first lock member further including a bore in close but sliding fit about said sheath, said bore being defined by a bridge slightly proximal of said ramp; and wherein said second lock member comprises an eyelet having an outer diameter greater than an inner diameter of said sheath and less than the diameter of said bore, said second lock member being located about said cannula within said first lock member.

35. A catheter assembly as set forth in claim 34, wherein said eyelet includes a distal end portion having a flange extending outwardly therefrom, the outer diameter of said flange being less than the inner diameter of said bore.

36. A catheter assembly as set forth in claim 1, wherein said first lock member includes said sheath stripping means, said sheath stripping means comprising a ramp positioned to slidingly receive said sheath distal end portion and to direct said sheath distal end portion outwardly away from said cannula as said sheath is moved distally, said first lock member further including a bore in close but sliding fit about said sheath, said bore being defined by a bridge slightly proximal of said ramp; and wherein said second lock member comprises an eyelet having an outer diameter greater than an inner diameter of said sheath and less than the diameter of said bore, said second lock member being located about said cannula within said first lock member.

* * * * *